(12) United States Patent
Zakharenko et al.

(10) Patent No.: US 10,308,933 B2
(45) Date of Patent: Jun. 4, 2019

(54) METHODS FOR DIAGNOSING AND TREATING LEARNING OR MENTAL DISORDERS

(71) Applicant: St. Jude Children's Research Hospital, Memphis, TN (US)

(72) Inventors: Stanislav S. Zakharenko, Collierville, TN (US); Laurie R. Earls, Memphis, TN (US)

(73) Assignee: ST. JUDE CHILDREN'S RESEARCH HOSPITAL, Memphis, TN (US)

(*) Notice: Subject to any disclaimer, the term of this patent is extended or adjusted under 35 U.S.C. 154(b) by 0 days.

(21) Appl. No.: 14/984,045

(22) Filed: Dec. 30, 2015

(65) Prior Publication Data

US 2016/0108402 A1 Apr. 21, 2016

Related U.S. Application Data

(63) Continuation of application No. 14/371,256, filed as application No. PCT/US2013/024257 on Feb. 1, 2013, now Pat. No. 9,255,268.

(60) Provisional application No. 61/593,947, filed on Feb. 2, 2012.

(51) Int. Cl.
*C12N 15/113* (2010.01)
*C12Q 1/6883* (2018.01)
*A61K 31/7105* (2006.01)

(52) U.S. Cl.
CPC ........ *C12N 15/113* (2013.01); *A61K 31/7105* (2013.01); *C12Q 1/6883* (2013.01); *C12N 2310/141* (2013.01); *C12N 2320/30* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2009/0192112 A1 | 7/2009 | Simeone et al. ............ 514/44 R |
| 2010/0009367 A1 | 1/2010 | Sommer et al. ............ 435/6.16 |
| 2010/0227908 A1 | 9/2010 | Cairns .......................... 514/44 A |
| 2014/0187608 A1* | 7/2014 | Gogos ............... C07K 14/4703 514/44 A |

FOREIGN PATENT DOCUMENTS

WO WO 2011/066132 A1 6/2011

OTHER PUBLICATIONS

Hauberg ME, et al. "Analyzing the Role of MicroRNAs in Schizophrenia in the Context of Common Genetic Risk Variants." JAMA Psychiatry. 2016;73(4):369-377. (Year: 2016).*
Mellios, et al. "The Emerging Role of microRNAs in Schizophrenia and Autism Spectrum Disorders." Frontiers in Psychiatry. 2012, v3:39. (Year: 2012).*
Bassett et al. "Clinical Features of 78 Adults With 22q11 Deletion Syndrome" American Journal of Medical Genetics Part A 2005 138(4):307-313.
Beveridge and Cairns "MicroRNA Dysregulation in Schizophrenia" Neurobiology of Disease 2012 46:263-271.
Burn et al. "Conotruncal Anomaly Face Syndrome is Associated with a Deletion within Chomosome 22q11" Journal of Medical Genetics 1993 30:822-824.
Chow et al. "Neurocognitive Profile in 22q11 Deletion Syndrome and Schizophrenia" Schizophrenia Research 2006 87(1-3):270-278.
Earls et al. "Dysregulation of Presynaptic Calcium and Synaptic Plasticity in a Mouse Model of 22q11 Deletion Syndrome" The Journal of Neuroscience 2010 30(47):15843-15855.
Earls et al. "Age-Dependent MicroRNA Control of Synaptic Plasticity in 22q11 Deletion Syndrome and Schizophrenia" The Journal of Neuroscience 2012 32(41):14132-14144.
Gold, J. M. "Cognitive Deficits as Treatment Targets in Schizophrenia" Schizophrenia Research 2004 72:21-28.
Green, M. F. "What Are the Functional Consequences of Neurocognitive Deficits in Schizophrenia?" The American Journal of Psychiatry 1996 153(3):321-330.
Green et al. "Neurocognitive Deficits and Functional Outcome in Schizophrenia: Are We Measuring the "Right Stuff"?" Schizophrenia Bulletin 2000 26(1):119-136.
Heckers et al. "Impaired Recruitment of the Hippocampus During Conscious Recollection in Schizophrenia" Nature Neuroscience 1998 1(4):318-323.
Lindsay et al. "Congenital Heart Disease in Mice Deficient for the DiGeorge Syndrome Region" Nature 1999 401:379-383.
Martin et al. "Synaptic Plasticity and Memory: An Evaluation of the Hypothesis" Annual Review of Neuroscience 2000 23:649-711.
Milner et al. "Cognitive Neuroscience and the Study of Memory" Neuron 1998 20:445-468.
Moreau et al. "Altered MicroRNA Expression Profiles in Post-Mortem Brain Samples from Individuals with Schizophrenia and Bipolar Disorder" Biological Psychiatry 2011 69(2):188-193.
Murphy et al. "High Rates of Schizophrenia in Adults with Velo-Cardio-Facial Syndrome" Archives of General Psychiatry 1999 56:940-945.
Òskarsdòttir et al. "Incidence and Prevalence of the 22q11 Deletion Syndrome: a Population-Based Study in Western Sweden" Archives of Disease in Childhood 2004 89:148-151.
Pulver et al. "Psychotic Illness in Patients Diagnosed with Velo-Cardio-Facial Syndrome and Their Relatives" 182(8):476-478 The Journal of Nervous and Mental Disorders 1994.
Rogaev, E.I. "Small RNAs in Human Brain Development and Disorders" Biochemistry 2005 70(12):1404-1407.
Ryan et al. "Spectrum of Clinical Features Associated with Interstitial Chromosome 22q11 Deletions: a European Collaborative Study" Journal of Medical Genetics 1997 34:798-804.
Scambler, P. J. and Kelly, D. "Velo-Cardio-Facial Syndrome Associated with Chromosome 22 Deletions Encompassing the DiGeorge Locus" Lancet 1992 339(8802):1138-1139.
Scambler, P. J. "The 22q11 Deletion Syndromes" Human Molecular Genetics 2000 9(16):2421-2426.

(Continued)

*Primary Examiner* — Jennifer Pitrak McDonald
(74) *Attorney, Agent, or Firm* — Licata & Tyrrell P.C.

(57) ABSTRACT

The present invention embraces methods for the diagnosis and treatment of learning or mental disorders such as schizophrenia using miR-25, miR-98, or miR-185.

4 Claims, No Drawings

Specification includes a Sequence Listing.

(56) References Cited

OTHER PUBLICATIONS

Sempere et al. "Expression Profiling of Mammalian MicroRNAs Uncovers a Subset of Brain-Expressed MicroRNAs with Possible Roles in Murine and Human Neuronal Differention" Genome Biology 2004 5:R13.
Smirnova et al. "Regulation of MiRNA Expression During Neural Cell Specification" European Journal of Neuroscience 2005 21(6):1469-1477.
Stark et al. "Altered Brain MicroRNA Biogenesis Contributes to Phenotypic Deficits in a 22q11-Deletion Mouse Model" Nature Genetics 2008 40(6):751-760.
Tamminga et al. "The Hippocampal Formation in Schizophrenia" The American Journal of Psychiatry 2010 167:1178-1193.
Weinberger et al. "Schizophrenia: New Phenes and New Genes" Biological Psychiatry 1999 46(1):3-7.
Xu et al. "Derepression of a Neuronal Inhibitor due to miRNA Dysregulation in a Schizophrenia-Related Microdeletion" Cell 2013 152:262-275.
microRNA.org Targets and Expression, Nov. 1, 2011 (Nov. 1, 2011) [online]. Retrieved from the internet: <URL: http://www.microrna.org/microrna/getMrna.do?gene=11938&utr=14414&organism=10090&matureName=mmu-miR-185#>. Especially p. 1.
Office Communication dated Mar. 6, 2015 from U.S. Appl. No. 14/371,256, filed Jul. 9, 2014.
Office Communication dated Jun. 16, 2015 from U.S. Appl. No. 14/371,256, filed Jul. 9, 2014.
Office Communication dated Sep. 17, 2015 from U.S. Appl. No. 14/371,256, filed Jul. 9, 2014.
Office Communication dated Oct. 21, 2015 from U.S. Appl. No. 14/371,256, filed Jul. 9, 2014.
International Search Report from PCT/US2013/024257, dated Apr. 9, 2013, PCT.
International Preliminary Report on Patentability from PCT/US2013/024257, dated Aug. 14, 2014, PCT.

* cited by examiner

METHODS FOR DIAGNOSING AND TREATING LEARNING OR MENTAL DISORDERS

This application is a continuation of U.S. Ser. No. 14/371,256 filed Jul. 9, 2014, which is the U.S. National Stage Application of PCT/US2013/024257 filed Feb. 1, 2013 and claims benefit of priority to U.S. Provisional Application Ser. No. 61/593,947, filed Feb. 2, 2012, the contents of each of which are incorporated herein by reference in their entirety.

INTRODUCTION

This invention was made with government support under grant MH079079 awarded by the National Institutes of Health. The government has certain rights in the invention.

BACKGROUND OF THE INVENTION

Schizophrenia is a devastating disease that affects approximately 1% of the world's population and is characterized by a constellation of symptoms that includes hallucinations and delusions (positive symptoms), antisocial behavior and blunted emotions (negative symptoms), and deficits in working memory, executive function, and learning and memory (cognitive symptoms). One of the best known genetic predictors of schizophrenia is the microdeletion disorder 22q11 deletion syndrome (22q11DS). This syndrome is caused by the hemizygous deletion of a 1.5- to 3-megabase region of the q arm of chromosome 22, resulting in the haploinsufficiency of 30 to 40 genes (Burn, et al. (1993) *J. Med. Genet.* 30:822; Ryan, et al. (1997) *J. Med. Genet.* 34:798; Scambler, et al. (2000) *Hum. Mol. Genet.* 9:2421; Oskarsdottir, et al. (2004) *Arch. Dis. Child* 89:148; Scambler, et al. (1992) *Lancet* 339:1138). Approximately 30% of children with 22q11DS experience schizophrenia or schizoaffective disorder during adolescence or early adulthood (Chow, et al. (2006) *Schizophr. Res.* 87:270; Pulver, et al. (1994) *J. Nerv. Ment. Dis.* 182:476; Bassett, et al. (2005) *Am. J. Med. Genet.* 138:307). Symptoms of 22q11DS-related schizophrenia are indistinguishable from those of the idiopathic disease (Pulver, et al. (1994) supra; Chow, et al. (2006) supra; Murphy, et al. (1999) *Arch. Gen. Psychiatry* 56:940), suggesting that the biological mechanisms involved in schizophrenia arising from the 22q11.2 deletion are the same as those involved in non-deletion-related schizophrenia.

Cognitive deficits are central to schizophrenia and are among the least treatable symptoms of the disease (Gold (2004) *Schizophr. Res.* 72:21; Green (1996) *Am. J. Psychiatry* 153:321; Green, et al. (2000) *Schizophr. Bull.* 26:119). These symptoms have been linked, in part, to the hippocampus (Heckers, et al. (1998) *Nat. Neurosci.* 1:318; Tamminga, et al. (2010) *Am. J. Psychiatry* 167:1178; Weinberger (1999) *Biol. Psychiatry* 46:3), a brain region well-studied for its role in learning and memory. Mechanisms of hippocampal learning and memory have been thoroughly characterized using animal models. Synaptic plasticity at excitatory synapses has emerged as a cellular mechanism of hippocampus-related learning and memory (Martin, et al. (2000) *Annu. Rev. Neurosci.* 23:649; Milner, et al. (1998) *Neuron* 20:445) and provides an excellent means to probe cellular events related to cognition in animal models of schizophrenia.

The 22q11DS-critical region of human chromosome 22 is largely conserved on mouse chromosome 16, allowing for the generation of 22q11DS mouse models. The Df(16)1/+ mouse carries a hemizygous deletion of 23 genes in the syntenic region of mouse chromosome 16 (Lindsay, et al. (1999) *Nature* 401:379) and develops a spatial memory deficit and enhanced synaptic plasticity in the form of long-term potentiation (LTP) by 16 weeks of age (Earls, et al. (2010) *J. Neurosci.* 30:15843). This age-dependent alteration in hippocampal synaptic plasticity is caused by an aberrant increase in the protein level of the sarco(endo)plasmic reticulum ATPase (SERCA2), which maintains calcium (Ca2+) levels in the endoplasmic reticulum (ER). SERCA2 upregulation leads to increased LTP by enhancing Ca2+ entry into presynaptic cytoplasm and releasing an excess of neurotransmitter during synaptic plasticity induction. Therefore, the age-dependent synaptic abnormalities in Df(16)1/+ mice may be relevant to the cognitive decline observed at the onset of schizophrenia. Identification of the culprit genes within the 22q11DS-critical region that cause these abnormalities provides insight into the pathophysiology of schizophrenia.

A survey of miRNA expression patterns in various organ and tissue types has identified several brain-specific and brain-enriched miRNAs (Sempere, et al. (2004) *Genome Biol.* 5:R13). There are a growing number of miRNAs with well-characterized neurodevelopmental functions. miR-124 and miR-9 influence the decision of neural precursors to adopt a neuronal or glial fate. miR-124 inhibits expression of nonneuronal genes and splicing factors, and transfecting miR-124 duplexes into progenitor cells decreases the number of cells expressing glial markers (glial fibrillary acidic protein) while increasing the number of neurons (Smirnova, et al. (2005) *J. Neurosci.* 21:1569-77). In addition, altered expression of selected miRNAs has been shown to correlate with schizophrenia or bipolar disorder (Moreau, et al. (2011) *Biol. Psychiatry* 69:188) and miRNAs, as well as proteins regulating the biogenesis of miRNAs (e.g., DGCR8), have been suggested for use in the diagnosis and prognosis of schizophrenia (US 2010/0227908 and US 2010/0009367).

SUMMARY OF THE INVENTION

The present invention features methods for reversing age-dependent changes in neural function and treating a learning disorder or mental disorder by administering to a subject in need of treatment an effective amount of at least one microRNA (miR) selected from the group of miR-25, miR-98 and miR-185. In certain embodiments, the mental disorder is a psychiatric disease such as schizophrenia, Alzheimer's disease, bipolar disorder, schizoaffective disorder, 22q11 deletion syndrome, attention-deficit hyperactivity disorder, obsessive-compulsive disorder or autism spectrum disorder.

An additional feature of this invention is a method for diagnosing the susceptibility for developing a learning or mental disorder by obtaining a biological sample from a subject, and measuring the level of at least one microRNA (miR) selected from the group of miR-25, miR-98 and miR-185 in said sample, wherein a reduced level of the miR as compared to a control indicates an increased susceptibility to developing a learning or mental disorder. In some embodiments, the mental disorder is a psychiatric disease such as schizophrenia, Alzheimer's disease, bipolar disorder, schizoaffective disorder, 22q11 deletion syndrome, attention-deficit hyperactivity disorder, obsessive-compulsive or autism spectrum disorder.

DETAILED DESCRIPTION OF THE INVENTION

Using a panel of mutant mice carrying hemizygous deletions of clusters of genes or individual genes within the 22q11DS-critical region, genes involved in the observed age-dependent increase in LTP were identified. This systematic screen identified Dgcr8 as a contributor to synaptic abnormalities. DGCR8 is a double-stranded RNA-binding protein that is involved in the early stages of microRNA (miR) biogenesis. The data presented herein show that the hemizygous loss of Dgcr8 causes an age-dependent increase in LTP that depends on upregulation of synaptic SERCA2. Three miRs (miR-25, -185, and -98) were found to be depleted with age in 22q11DS mouse models and are predicted to target the Serca2 transcript. Indeed, restoration of these miRs to mature hippocampus was sufficient to rescue aberrant LTP observed in Dgcr8$^{+/-}$ mice. In addition, it has now been shown that SERCA2 is also upregulated in postmortem brain samples from patients with schizophrenia. Therefore, the molecular events described in the mouse model of 22q11DS are of relevance to the mechanisms of the human disease. Accordingly, the present invention embraces methods for reversing age-dependent changes in neural function, and treating and diagnosing learning or mental disorders using miR-25, miR-185, and miR-98.

As used herein interchangeably, a "miR gene product," "microRNA," "miR," or "miRNA" refers to the unprocessed or processed RNA transcript from a miR gene. As the miR gene products are not translated into protein, the term "miR gene products" does not include proteins. The unprocessed miR gene transcript is also called a "miR precursor," and is typically an RNA transcript of about 70-100 nucleotides in length. The miR precursor can be processed by digestion with an RNAse (for example, Dicer, Argonaut, RNAse III (e.g., $E.$ $coli$ RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

MicroRNA can be modified in accordance with the invention using any suitable chemical moiety including, for example, phosphorothioate, boranophosphate, 2'-O-methyl, 2'-fluoro, PEG, terminal inverted-dT base, locked nucleic acids (LNA), peptide nucleic acids (PNAs), 2'-fluoro N3-P5'-phosphoramidites, 1,5'-anhydrohexitol nucleic acids (HNAs), or combinations thereof. In particular embodiments, the miRNA is modified to include LNA. In a comparison of LNA-DNA-LNA gapmers with siRNAs, phosphorothioate and 2'-O-methyl RNA-DNA gapmers against expression of the vanilloid receptor subtype 1 (VR1) in Cos-7 cells, it was shown that LNA-DNA-LNA gapmers having a 5nt-8nt-5nt design were 175- and 550-fold superior in suppressing VR1 compared to isosequential phosphorothioate and 2'-Ome oligonucleotides respectively (Grunweller, et al. (2003) $NAR$ 31:3185-93).

LNAs, often referred to as inaccessible RNA, are modified RNA nucleotides that can be placed either 5' or internally. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. Such oligomers are commercially available. The locked ribose conformation enhances base stacking and backbone pre-organization. This significantly increases the thermal stability (melting temperature) of oligonucleotides (Kaur, et al. (2006) $Biochemistry$ 45(23):7347-55). LNA bases may be included in a backbone of LNA, 2'-O-methyl RNA, 2'-methoxyethyl RNA, or 2'-fluoro RNA. These molecules may utilize either a phosphodiester or phosphorothioate backbone.

The microRNAs of the invention and the sequences thereof are well-known in the art and can be found in the miRBase Sequence Database and Registry (Kozomara & Griffiths-Jones (2011) $Nucl.$ $Acids$ $Res.$ 39:D152-7; Griffiths-Jones, et al. (2008) $Nucl.$ $Acids$ $Res.$ 36:D154-8; and Griffiths-Jones (2004) $Nucl.$ $Acids$ $Res.$ 32:D109-111. For example, human miR-25 (Gene ID 407014) has a precursor sequence of GGC CAG UGU UGA GAG GCG GAG ACU UGG GCA AUU GCU GGA CGC UGC CCU GGG CAU UGC ACU UGU CUC GGU CUG ACA GUG CCG GCC (SEQ ID NO:1) and mature sequence of CAU UGC ACU UGU CUC GGU CUG A (SEQ ID NO:2). Human miR-98 (Gene ID 407054) has a precursor sequence of AGG AUU CUG CUC AUG CCA GGG UGA GGU AGU AAG UUG UAU UGU UGU GGG GUA GGG AUA UUA GGC CCC AAU UAG AAG AUA ACU AUA CAA CUU ACU ACU UUC CCU GGU GUG UGG CAU AUU CA (SEQ ID NO:3) and a mature sequence of UGA GGU AGU AAG UUG UAU UGU U (SEQ ID NO:4). Human miR-185 (Gene ID 406961) has a precursor sequence of AGG GGG CGA GGG AUU GGA GAG AAA GGC AGU UCC UGA UGG UCC CCU CCC CAG GGG CUG GCU UUC CUC UGG UCC UUC CCU CCC A (SEQ ID NO:5) and mature sequence of UGG AGA GAA AGG CAG UUC CUG A (SEQ ID NO:6).

As demonstrated herein, administration of miR-25, miR-185, and miR-98 to Dgcr8$^{+/-}$ mice was sufficient to rescue aberrant LTP, a key cellular aspect of neural function. Therefore, the present includes methods for restoring, reversing or stabilizing age-dependent changes, in particular age-dependent decreases, in neural function and treating a learning or mental disorder by administering an effective amount of at least one of miR-25, miR-185 and miR-98 to a subject in need of such treatment.

As is known in the art, long-term potentiation or LTP is a long-lasting enhancement in signal transmission between two neurons that results from stimulating them synchronously (Cooke & Bliss (2006) $Brain$ 129 (Pt 7): 1659-73). At a cellular level, LTP enhances synaptic transmission. It improves the ability of two neurons, one presynaptic and the other postsynaptic, to communicate with one another across a synapse. LTP is widely considered one of the major cellular mechanisms that underlies learning and memory (Cook & Bliss (2006) supra; Bliss & Collingridge (1993) $Nature$ 361:31-9) and is a key aspect of neural function.

As used herein, "treating" or "treatment" of a disease or disorder refers to arresting, reducing, ameliorating or delaying the onset of a disease, disorder, or at least one clinical symptom or physical parameter of a disease or disorder, which may or may not be discernible by the patient. In certain embodiments, "treating" or "treatment" refers to inhibiting or controlling the disease or disorder, either physically (e.g., stabilization of a discernible symptom), physiologically (e.g., stabilization of a physical parameter), or both. As used herein, an "effective amount" of a miR gene product is an amount sufficient to measurably restore or reverse age-dependent decreases in neural function. Alternatively stated, an effective amount of a miR gene product measurably restores, reverses or stabilizes neural function to normal levels or levels observed younger subjects. One skilled in the art can readily determine an effective amount of a miR gene product to be administered to a given subject, by taking into account factors, such as the size and weight of the subject; health and sex of the subject; the route of administration; and whether the administration is regional or systemic. In addition, one skilled in the art can readily determine an appropriate dosage regimen for the administration of an isolated miR gene product to a given subject. For example, a miR gene product can be administered to the subject once (e.g., as a single injection or deposition). Alternatively, a miR gene product can be administered multiple times to a subject. Where a dosage regimen includes multiple administrations, it is understood that the effective amount of the miR gene product administered to the subject can include the total amount of gene product administered over the entire dosage regimen.

In some embodiments, the miR gene product is isolated. As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating a learning or mental disorder in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo.), Pierce Chemical (part of Perbio Science, Rockford, Ill.), Glen Research (Sterling, Va.), ChemGenes (Ashland, Mass.) and Cruachem (Glasgow, UK).

Alternatively, the miR gene products can be expressed from recombinant vectors, either individually or from the same or different vector. Recombinant vectors include circular or linear DNA plasmids and typically contain a suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also include inducible or regulatable promoters for expression of the miR gene products in brain cells.

The miR gene products that are expressed from recombinant plasmids can be isolated from cultured cell expression systems by standard techniques. The miR gene products that are expressed from recombinant plasmids can also be delivered to, and expressed directly in, the cells of interest. In one embodiment, the miR gene products are expressed as RNA precursor molecules, and the precursor molecules are processed into the functional miR gene products by a suitable processing system, including, but not limited to, processing systems extant within, e.g., a hippocampal cell. Other suitable processing systems include, e.g., the in vitro *Drosophila* cell lysate system (e.g., as described in US 2002/0086356) and the *E. coli* RNAse III system (e.g., as described in US 2004/0014113).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng, et al. (2002) *Molecular Cell* 9:1327-1333; Tuschl (2002) *Nat. Biotechnol.* 20:446-448; Brummelkamp, et al. (2002) *Science* 296:550-553; Miyagishi, et al. (2002) *Nat. Biotechnol.* 20:497-500; Paddison, et al. (2002) *Genes Dev.* 16:948-958; Lee, et al. (2002) *Nat. Biotechnol.* 20:500-505; and Paul, et al. (2002) *Nat. Biotechnol.* 20:505-508.

In one embodiment, a plasmid expressing the miR gene products includes a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. The RNA expressed from the recombinant viral vectors can either be isolated from cultured cell expression systems by standard techniques, or can be expressed directly in brain cells.

The recombinant viral vectors of the invention include sequences encoding the miR gene products and any suitable promoter for expressing the RNA sequences. Suitable promoters include, but are not limited to, the U6 or H1 RNA pol III promoter sequences, the cytomegalovirus promoters, or more particularly a neuron-specific promoter such as the Synapsin promoter. Selection of other suitable promoters is within the skill in the art.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, et al. (2002) *J. Virol.* 76:791-801.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995) *Gene Therap.* 2:301-310;

Eglitis (1988) *Biotechniques* 6:608-614; Miller (1990) *Hum. Gene Therap.* 1:5-14; and Anderson (1998), *Nature* 392:25-30).

Particularly suitable viral vectors are those derived from AV and AAV. A suitable AV vector for expressing the miR gene products, a method for constructing the recombinant AV vector, and a method for delivering the vector into target cells, are described in Xia, et al. (2002) *Nat. Biotech.* 20:1006-1010. Suitable AAV vectors for expressing the miR gene products, methods for constructing the recombinant AAV vector, and methods for delivering the vectors into target cells are described in Samulski, et al. (1987) *J. Virol.* 61:3096-3101; Fisher, et al. (1996) *J. Virol.* 70:520-532; Samulski, et al. (1989) *J. Virol.* 63:3822-3826; U.S. Pat. Nos. 5,252,479; 5,139,941; WO 94/13788; and WO 93/24641. In one embodiment, the miR gene products are expressed from a recombinant AAV vector including neuron-specific Synapsin promoter.

Isolated miR gene products, either alone or in combination, can be formulated in pharmaceutical compositions suitable for administration to a subject in need of treatment. Such compositions typically contain from about 0.1 to 90% by weight (such as 1 to 20% or 1 to 10%) of the miR gene product in a pharmaceutically acceptable carrier. A pharmaceutically acceptable carrier is a material useful for the purpose of administering the medicament, which is preferably sterile and non-toxic, and can be solid, liquid, or gaseous materials, which is otherwise inert and medically acceptable, and is compatible with the active ingredients. A generally recognized compendium of methods and ingredients of pharmaceutical compositions is Remington: The Science and Practice of Pharmacy, Alfonso R. Gennaro, editor, 20th ed. Lippincott Williams & Wilkins: Philadelphia, Pa., 2000.

The pharmaceutical compositions (including isolated miR gene products or vectors encoding the same) can be administered to the subject being treated by any, or a combination, of several routes, such as oral, intravenous, trans-mucosal (e.g., nasal, vaginal, etc.), pulmonary, transdermal, ocular, buccal, sublingual, intraperitoneal, intrathecal, intramuscular, interstitial, intraventricular, intrathecal or long-term depot preparation. Solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid. Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the subject to be treated.

Injectable compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active agent(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like. As yet a further alternative, the instant miR gene products can be delivered by biodegradable polymer wafers, microspheres, or nanoparticles.

Subjects benefiting from treatment with instant methods include those having, those suspected of having or those predisposed to have (e.g., genetic predisposition) a learning disorder or mental disorder. Learning disorders include childhood learning disorders, wherein the subject has an impaired ability to learn. Such learning disorders can be diagnosed by using the DSM-IV criteria (APA, 1994, Diagnostic and Statistical Manual of Mental Disorders (Fourth Edition), Washington, D.C.). Mental disorders embraced by the present invention include, but are not limited to psychiatric diseases such as schizophrenia, Alzheimer's disease, bipolar disorder, schizoaffective disorder, 22q11 deletion syndrome, attention-deficit hyperactivity disorder, obsessive-compulsive disorder and autism spectrum disorder.

As used herein, the term "schizophrenia" refers to a psychiatric disorder that includes at least two of the following: delusions, hallucinations, disorganized speech, grossly disorganized or catatonic behavior, or negative symptoms. Subjects can be diagnosed as schizophrenic using the DSM-IV criteria.

The term "Alzheimer's Disease" refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Methods for diagnosing Alzheimer's Disease are known in the art. For example, the National Institute of Neurological and Communicative Disorders and Stroke-Alzheimer's Disease and the Alzheimer's Disease and Related Disorders Association (NINCDS-ADRDA) criteria can be used to diagnose Alzheimer's Disease (McKhann, et al. (1984) *Neurology* 34:939-944). The patient's cognitive function can be assessed by the Alzheimer's Disease Assessment Scale-cognitive subscale (ADAS-cog; Rosen, et al. (1984) *Am. J. Psychiatry* 141:1356-1364).

Bipolar disorder, also known as manic depressive disorder, manic depression or bipolar affective disorder, is a psychiatric diagnosis that describes a category of mood disorders defined by the presence of one or more episodes of abnormally elevated mood clinically referred to as mania or, if milder, hypomania. Individuals who experience manic episodes also commonly experience depressive episodes or symptoms, or mixed episodes in which features of both mania and depression are present at the same time. These episodes are usually separated by periods of "normal" mood, but in some individuals, depression and mania may rapidly alternate, known as rapid cycling. Extreme manic episodes can sometimes lead to psychotic symptoms such as delusions and hallucinations. Subjects can be diagnosed as having bipolar disorder using the DSM-IV-TR criteria and the World Health Organization's International Statistical Classification of Diseases and Related Health Problems, the ICD-10.

Schizoaffective disorder is a psychiatric diagnosis that describes a mental disorder characterized by recurring episodes of mood disorder and psychosis. Distortions in perception alternate with and occur simultaneously with elevated or depressed mood. These perceptual distortions may affect all five senses, including sight, hearing, taste, smell and touch, but most commonly manifest as auditory hallucinations, paranoid or bizarre delusions, or disorganized speech and thinking with significant social or occupational dysfunction. Subjects can be diagnosed as having a schizoaffective disorder using the DSM-IV-TR criteria.

Characteristic signs and symptoms of 22q11 deletion syndrome may include birth defects such as congenital heart disease, defects in the palate, most commonly related to neuromuscular problems with closure (velo-pharyngeal insufficiency), learning disabilities, mild differences in facial features, and recurrent infections. 22q11 deletion syndrome may be first spotted when an affected newborn has heart defects or convulsions from hypocalcemia due to malfunctioning the parathyroid glands and low levels of parathyroid hormone (parathormone). Affected individuals may also have any other kind of birth defect including kidney abnormalities and significant feeding difficulties as babies. Autoimmune disorders such as hypothyroidism and hypoparathyroidism or thrombocytopenia (low platelet levels), and psychiatric illnesses are common late-occurring features. Diagnosis of 22q11 deletion syndrome is typically determined by the presence of the 22q11.2 microdeletion.

The term "attention-deficit hyperactivity disorder attention deficit disorder," as used herein, refers to a disorder that is most commonly exhibited by children and which can be characterized by increased motor activity and a decreased attention span. The DSM-IV criteria can be used to diagnose attention deficit disorder.

Obsessive-compulsive disorder (OCD) is a mental disorder characterized by intrusive thoughts that produce anxiety, by repetitive behaviors aimed at reducing anxiety, or by combinations of such thoughts (obsessions) and behaviors (compulsions). The symptoms of this anxiety disorder range from repetitive hand-washing and extensive hoarding to preoccupation with sexual, religious, or aggressive impulses as well as corrections of minor things. These symptoms can be alienating and time-consuming, and often cause severe emotional and economic loss. Although the acts of those who have OCD may appear paranoid and come across to others as psychotic, OCD sufferers often recognize their thoughts and subsequent actions as irrational, and they may become further distressed by this realization.

As used herein, the term "autism spectrum disorder" refers to a spectrum of psychological conditions characterized by widespread abnormalities of social interactions and communication, as well as severely restricted interests and highly repetitive behavior. Subjects with autism experience mental introversion characterized by morbid self-absorption, social failure, language delay, and stereotyped behavior. The three main forms of ASD are Autism, Asperger syndrome, Pervasive Developmental Disorder Not Otherwise Specified (PDD-NOS), sometimes called atypical autism. Patients can be diagnosed as suffering from autism by using the DSM-IV criteria.

Subjects to be treated in accordance with the instant method can be provided with an effective amount of a miR gene product as described herein. Where appropriate, a pharmaceutical composition containing a miR gene product can be administered to a subject suffering from learning or mental disorder along with, or in sequence with, an art-known drug for treating the learning or mental disorder. For example, art-known drugs for treating schizophrenia, include olanzapine, clozapine, haloperidol, and the like. Similarly, a miR gene product can be used in combination with, or in sequence with, other art-known antipsychotics (e.g., "typical," "atypical," and depot antipsychotics for treating schizophrenia and other psychotic conditions), psychostimulants (for treating attention deficit disorder or learning disorders), or Alzheimer's disease therapeutics (for treating Alzheimer's disease). Such pharmaceutical compositions are included within the invention. In general, the antipsychotic, psychostimulant, or Alzheimer's disease therapeutic typically is administered at a dosage of 0.25-5000 mg/d (e.g., 5-1000 mg/d)). "Typical" antipsychotics are conventional antipsychotics such as phenothiazine, butryophenones, thioxanthenes, dibenzoxazepines, dihydroindolones, and diphenylbutylpiperidines. "Atypical" antipsychotics are a new generation of antipsychotics which generally act on the dopamine $D_2$ and $5HT_2$ serotonin receptor and have high levels of efficacy and a benign extrapyramidal symptom side effect profile. Examples of typical antipsychotics include Chlorpromazine, Thioridazine, Mesoridazine, Fluphenazine, Perphenazine, Trifluoperazine, Thiothixene, Haloperidol, Loxapine, Molindone, Acetophenazine, Droperidol, Pimozide. Examples of atypical antipsychotics include Clozapine, Risperidone, Olanzapine, and Quetiapine. Depot antipsychotics also can be used, e.g., Haloperidol decanoate, Fluphenazine decanoate, and Fluphenazine enanthate. Additional antipsychotics include Butaperazine, Carphenazine, Remoxipride, Piperacetazine, Sulpiride, and Ziprasidone. Psychostimulants that are particularly useful for treating attention deficit disorder include Dextroamphetamine, Methamphetamine, Methylphenidate, and Pemoline. Examples of Alzheimer's disease therapeutics that can be used in the invention include Donepezil and Tacrine. Thus, the invention also provides pharmaceutical compositions that contain one or more miR gene products along with an antipsychotic, psychostimulant, or Alzheimer's disease therapeutic.

In addition to, or as an alternative to, conventional methods of diagnosing a subject for a learning disorder or mental disorder, the present invention also embraces a method for diagnosing an increased susceptibility to developing a learning or mental disorder based upon the levels of one or more of miR-25, miR-98 or miR-185. In accordance with the diagnostic method of the invention, a biological sample is obtained from a subject to be tested, and the level of the miR gene product in said sample is measured and compared to a control, wherein a reduced or decreased level of the miR gene product as compared to the control indicates an increased susceptibility to developing a learning or mental disorder. As used herein, a "subject" can be any mammal that has, or is suspected of having, a learning or mental disorder. In a preferred embodiment, the subject is a human who has, or is suspected of having, a learning or mental disorder.

The level of at least one miR gene product can be measured in cells of a biological sample obtained from the subject. For example, a tissue sample can be removed from a subject suspected of having, or susceptible to developing, a learning or mental disorder by conventional biopsy techniques. A corresponding control tissue sample, or a control reference sample, can be obtained from unaffected tissues of the subject, from a normal human individual or population of normal individuals, or from cultured cells corresponding to the majority of cells in the subject's sample. The control tissue sample is then processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

In one embodiment, the level of the at least one miR gene product in the test sample is less than the level of the corresponding miR gene product in the control sample (i.e., expression of the miR gene product is "down-regulated"). As used herein, expression of a miR gene product is "down-regulated" when the amount of miR gene product in a cell or tissue sample from a subject is less than the amount of the same gene product in a control cell or tissue sample. The relative miR gene expression in the control and normal samples can be determined with respect to one or more RNA expression standards. The standards can include, for example, a zero miR gene expression level, the miR gene expression level in a standard cell line, the miR gene expression level in unaffected tissues of the subject, or the average level of miR gene expression previously obtained for a population of normal human controls. A decrease in the level of a miR gene product in the sample obtained from the subject, relative to the level of a corresponding miR gene product in a control sample, is indicative of a learning or mental disorder in the subject.

The diagnostic methods of the invention can be used in the initial determination of whether a subject has a learning or mental disorder or in the confirmation of a diagnosis based upon conventional behavioral or clinical analysis. In this respect, subjects benefiting from the instant diagnostic methods include those suspected of having, or those predisposed (e.g., based upon heredity) to have a learning or mental disorder.

As with the method of treatment, learning or mental disorders that can be diagnosed in accordance with the instant diagnostic methods include, but are not limited to, having, suspected of having or those predisposed to have schizophrenia, Alzheimer's disease, bipolar disorder, schizoaffective disorder, 22q11 deletion syndrome, attention-deficit hyperactivity disorder, obsessive-compulsive disorder or autism spectrum disorder.

The invention is described in greater detail by the following non-limiting examples.

EXAMPLE 1

Age-Dependent LTP Increase in Dgcr8$^{+/-}$ Mice

In Df(16)1/+ mice, LTP of synaptic transmission measured at excitatory hippocampal synapses between CA3 and CA1 pyramidal neurons (CA3-CA1 synapses) is increased in mature (16-20 weeks) but not young (8-10 weeks) animals (Earls, et al. (2010) supra). To narrow the location of genes involved in the LTP phenotype, mice that carry smaller hemizygous subdeletions within the Df(16)1 region were analyzed (Kimber, et al. (1999) Hum. Mol. Genet. 8:2229; Lindsay, et al. (2001) Nature 410:97). LTP of field excitatory postsynaptic potentials (fEPSPs) was tested in acute hippocampal slices from Df(16)2/+ mice, which carry a hemizygous deletion of genes at the proximal end of the Df(16)1 region (Es2el-Trxr2). As in Df(16)1/+ mice, LTP was elevated in Df(16)2/+ animals in an age-dependent fashion. Thus, fEPSPs measured six hours after induction of LTP showed no significant difference between young Df(16) 2/+ and wild-type (WT) littermates (Df(16)2/+: 20 slices, 4 mice; WT: 23 slices, 5 mice; p=0.238). However, LTP was significantly higher in mature Df(16)2/+ mice than in WT littermates (Df(16)2/+: 22 slices, 6 mice; WT: 27 slices, 7 mice; p=0.006). As is the case with Df (16)1/+ mice (Earls, et al. (2010) supra), the increase in LTP in mature Df(16)2/+ mice was not due to altered basal synaptic transmission, because the input-output relationship between fEPSPs and stimulation intensity was comparable between young and mature Df(16)2/+ and WT mice. These results indicate that the hemizygous deletion of a gene within the Df(16)2 region contributes to the LTP increase observed in mouse models of 22q11DS.

To further narrow the LTP-critical region, LTP was measured in Znf741-Ctp/+ mice (Kimber, et al. (1999) supra), which carry a hemizygous, 150-kilobase subdeletion that includes the three most proximal Df(16)2 genes, Es2e1, Gsc1, and Ctp. LTP was normal in mature Znf741-Ctp/+ mice, indicating that Es2e1, Gsc1, and Ctp do not contribute to the phenotype observed in Df(16)2/+ mice. Among the remaining genes in the Df(16)2 region, five have been previously implicated in the pathogenesis of 22q11DS and schizophrenia. To test their contribution to age-dependent LTP, mice deficient for those genes were analyzed. These included Zdhhc8$^{+/-}$ and Dgcr8$^{+/-}$ mice, which were produced during this study, and Comt$^{+/-}$ (Gogos, et al. (1998) Proc. Natl. Acad. Sci. USA 95:9991), Prodh$^{+/-}$ (Gogos, et al. (1999) Nat. Genet. 21:434), and Rtn4r$^{+/-}$ (Kim, et al. (2004) Neuron 44:439) mice. A comparison of LTP between the mutants and WT littermates at 16 weeks of age revealed an LTP increase only in Dgcr8$^{+/-}$ mice. Mature Dgcr8$^{+/-}$ mice demonstrated enhanced LTP equivalent to that of Df(16)2/+ mutants (Dgcr8$^{+/-}$: 29 slices, 6 mice; WT: 32 slices, 7 mice, p<0.001). Furthermore, similar to that in Df(16)2/+ mice, the LTP increase in Dgcr8$^{+/-}$ mutants was age-dependent; no increase was observed in 8- to 10-week-old animals (Dgcr8$^{+/-}$:31 slices, 7 mice; WT: 39 slices, 7 mice, p=0.850). Input-output coupling was not different between mature Dgcr8$^{+/-}$ and WT littermates, indicating that hemizygous deletion of Dgcr8 affects LTP but not basal synaptic transmission. These results implicate Dgcr8 deficiency as a contributing factor to the cognitive abnormalities observed in mouse models of 22q11DS.

EXAMPLE 2

Age-Dependent Upregulation of SERCA2 in the Dgcr8$^{+/-}$ Hippocampus

Age-dependent overexpression of SERCA2 is crucial for the LTP increase observed in Df(16)1/+ mice (Earls, et al. (2010) supra). SERCA2 is increased in the hippocampus of mature but not young Df(16)1/+ mice, and SERCA inhibitors rescue the LTP increase in mature Df(16)1/+ mice (Earls, et al. (2010) supra). Therefore, SERCA2 protein levels were determined in the hippocampus of young and mature Dgcr8$^{+/-}$ mice. Although no difference in SERCA2 levels was observed between Dgcr8$^{+/-}$ and WT whole-hippocampus extracts, SERCA2 protein levels in synaptosomal preparations from the hippocampus of mature Dgcr8$^{+/-}$ mice was significantly higher than that in WT littermates (p<0.001). In contrast, this synaptic increase in SERCA2 levels was not present in younger mice, indicating a correlation between SERCA2 elevation and LTP increase in Dgcr8$^{+/-}$ mice.

To test whether this increase in SERCA2 was necessary for enhanced LTP in Dgcr8$^{+/-}$ mice, LTP was measured in the presence of the SERCA inhibitor thapsigargin (4 µM). SERCA inhibition rescued the LTP increase in Dgcr8$^{+/-}$ slices to WT levels. In the absence of thapsigargin, LTP measured six hours after induction was approximately 120% stronger than in the presence of thapsigargin in slices from Dgcr8$^{+/-}$ mice (8 mice: 21 slices vehicle, 21 slices thapsigargin; p=0.014). As previously shown (Earls, et al. (2010) supra), thapsigargin did not affect LTP measured in slices from WT littermates (8 mice: 24 slices vehicle, 19 slices thapsigargin; p=0.974). Furthermore, in the presence of thapsigargin, LTP in Dgcr8$^{+/-}$ mice did not significantly differ from that in WT animals (p=0.854). These results indicate that SERCA2 is necessary for the observed LTP increase in mature Dgcr8$^{+/-}$ hippocampus.

EXAMPLE 3

Identification of MicroRNAs Responsible for Enhanced LTP in Mouse Models of 22q11DS Dgcr8 is a miR biogenesis gene, and miRs typically act as negative regulators of protein translation. DGCR8 binds to primary miR transcript hairpins and recruits the nuclease DROSHA, which cleaves the hairpins. Further processing produces mature miRs that bind to complementary seed sites in the 3'-untranslated regions (3'-UTRs) of target mRNA transcripts and negatively regulate protein translation through recruitment of the RNA-induced silencing complex (Bartel (2009) *Cell* 136:215). It was therefore determined whether SERCA2 is upregulated in 22q11DS brains due to the progressive loss of specific miRs. To identify potentially responsible miRs, a microarray comparison of hippocampal miRs was performed between Df(16)1/+ and WT littermates (7 mice per genotype). These experiments were carried out at 16 weeks, the age of onset of the LTP and SERCA2 increases. Fifty miRs were significantly reduced in the Df(16)1/+ mutants. These included miR-532-3p, miR-338-3p, miR-485, miR-341, miR-186, miR-23b, miR-25, miR-28, miR-532-5p, miR-582-5p, miR-872, miR-411, miR-380-3p, miR-873, miR-340-3p, miR-151-5p, miR-361, miR-342-3p, miR-409-5p, miR-409-3p, miR-425, miR-379, miR-337-5p, miR-185, miR-299*, miR-672, miR-323-3p, miR-541, miR-467b, miR-337-3p, miR-98, miR-382, miR-411*, miR-139-5p, miR-192, miR-377, miR-15b, miR-350, miR-331-3p, miR-676, miR-22*, miR-674*, miR-374, miR-329, miR-874, miR-421, miR-335-3p, miR-423-5p, miR-378 and miR-378*. Using qPCR, the depletion of mature forms of these miRs was verified in the Df(16)1/+ hippocampus. For a subset of these miRs, their depletion was also verified in the Dgcr8$^{+/-}$ hippocampus at 16 weeks.

MiRs affect their target mRNAs by binding to complementary seed sites within the 3'-UTR and recruiting the RNA-induced silencing complex to the transcript to prevent translation (Ambros (2004) *Nature* 341:350). Using the miR-target-prediction algorithms miRBase (Enright, et al. (2003) *Genome Biol.* 5:R1), TargetScan (Lewis, et al. (2005) *Cell* 120:15), DIANA-microT v3.0 (Kiriakidou, et al. (2004) *Genes Dev.* 18:1165), and miRDB (Wang & El Naga (2008) *Bioinformatics* 24:325), potential seed sites for miRs within the 3'UTR of the murine Serca2 transcript were identified. Of the miRs depleted in the 22q11DS mice, three were predicted to target the SERCA2 3'UTR: miR-25, -98, and -185. Depletion of mature forms of miR-25 and miR-185 in Df(16)1/+ mice was also verified using qPCR. However, depletion of mature miR-98 in Df(16)1/+ mice could not be determined due to the AT-rich nature of this miR. However, it was posited that the depletion of any of these miRs contributes to SERCA2 upregulation and abnormal LTP in 22q11DS mouse models.

EXAMPLE 4

Rescue of the LTP Increase in Dgcr8$^{+/-}$ Mice by Presynaptic Restoration of miR-25 or miR-185

To test whether depletion of miR-25 and miR-185 is required for the observed LTP increase in 22q11DS models, miR-25 or miR-185 were restored in hippocampal neurons of Dgcr8$^{+/-}$ mice to rescue the LTP phenotype. To do this, recombinant adeno-associated viruses (AAV) were generated that encode GFP and either miR-25 or miR-185 under control of the neuron-specific Synapsin promoter to infect adult neurons in vivo. Because the increase in LTP measured at CA3-CA1 synapses in mature Df(16)1/+ hippocampus is caused by presynaptic abnormalities (Earls, et al. (2010) supra), virus was injected into the CA3 region of the hippocampus in vivo. Injections were performed at 10 weeks of age, before the onset of LTP abnormalities. AAV expressing a given miR as injected into one hemisphere and an empty AAV (expressing only GFP) into the contralateral hemisphere as a control. LTP was then measured in both miR-injected and control-injected hippocampi at 16 weeks. AAV-driven GFP expression was robust in presynaptic CA3 neurons, but GFP was absent from postsynaptic CA1 neurons. Using qPCR, it was determined that the levels of miR-25 or miR-185 were elevated following injection of AAV-miR-25 or AAV-miR-185, respectively, but not following injection of the control AAV. Because miR levels were measured throughout the hippocampus, whereas the rescue viruses were only injected in the CA3 region, the levels of miRs measured in these experiments were an underestimate. Presynaptic expression of either miR-25 or miR-185 was sufficient to rescue the increased LTP in the Dgcr8$^{+/-}$ hippocampus. These results indicate that presynaptic depletion of SERCA2-targeting miRs causes the LTP increase in 22q11 mouse models, and restoration of any of these miRs is sufficient to rescue this abnormality in synaptic plasticity.

EXAMPLE 5

Elevation of SERCA2 in Postmortem Brain Tissue from Patients with Schizophrenia

It was previously shown that SERCA2 is elevated in the hippocampus of the Df(16)1/+ mouse model of 22q11DS (Earls, et al. (2010) supra). However, the hippocampus is clearly not the only brain region involved in psychiatric disease associated with the deletion. To determine the specificity of this upregulation, SERCA2 levels were tested in various Df(16)1/+ tissues. SERCA2 was elevated in various brain regions of Df(16)1/+ mice, including the cortex (125.2%±5.6% of the WT level, p=0.012; 4 mice per genotype) and cerebellum (124.6%±7.5% of the WT level, p=0.048; 4 mice per genotype), but not in non-neural tissues such as liver (96.9%±4.7% of the WT level, p=0.689; 3-4 mice per genotype). These findings indicate that changes in SERCA2 expression are brain-specific and found throughout the brain.

Because the elevation of SERCA2 has serious consequences on neural function, it was determined whether the molecular findings in the 22q11DS mouse models would translate to human disease. Therefore, SERCA2 levels were compared in postmortem tissue samples from the hippocampus and prefrontal cortex of patients with schizophrenia and unaffected controls. This comparison revealed a significant increase in SERCA2 levels in both brain regions of schizophrenic patients. This finding indicates that elevation in SERCA2 protein contributes to the symptoms of schizophrenia. The seed sites for hsa-miR-25, hsa-miR-98, and hsa-miR-185 are conserved in the 3'-UTR of human SERCA2B, indicating that modulation by these miRs is a potential mechanism of SERCA2 protein overexpression in schizophrenia.

What is claimed is:

1. A method for improving hippocampal synaptic plasticity comprising administering to a subject exhibiting an age-dependent alteration in synaptic plasticity an effective amount of microRNA (miR)-98 in combination with an antipsychotic, psychostimulant or Alzheimer's disease therapeutic thereby improving the subject's hippocampal synaptic plasticity.

2. A method for treating a mental disorder comprising administering to a subject having a 22q11 deletion syndrome, schizophrenia, or autism spectrum disorder an effective amount of microRNA (miR) -98 in combination with an antipsychotic, psychostimulant or Alzheimer's disease therapeutic thereby treating the subject's mental disorder.

3. A method for improving hippocampal synaptic plasticity comprising administering to a subject exhibiting an age-dependent alteration in synaptic plasticity an effective amount of microRNA (miR)-25 in combination with an antipsychotic, psychostimulant or Alzheimer's disease therapeutic thereby improving the subject's hippocampal synaptic plasticity.

4. A method for treating a mental disorder comprising administering to a subject having 22q11 deletion syndrome, schizophrenia, or autism spectrum disorder an effective amount of microRNA (miR)-25 in combination with an antipsychotic, psychostimulant or Alzheimer's disease therapeutic thereby treating the subject's mental disorder.

\* \* \* \* \*

SEQUENCE LISTING

```
<160> NUMBER OF SEQ ID NOS: 45

<210> SEQ ID NO 1
<211> LENGTH: 84
<212> TYPE: RNA
<213> ORGANISM: Homo sapiens

<400> SEQUENCE: 1
ggccaguguu gagaggcgga gacuugggca auugcuggac gcugcccugg gcauugcacu      60
ugucucgguc ugacagugcc ggcc                                            84

<210> SEQ ID NO 2
<211> LENGTH: 22
<212> TYPE: RNA
<213> ORGANISM: Homo sapiens

<400> SEQUENCE: 2
cauugcacuu gucucggucu ga                                              22

<210> SEQ ID NO 3
<211> LENGTH: 119
<212> TYPE: RNA
<213> ORGANISM: Homo sapiens

<400> SEQUENCE: 3
aggauucugc ucaugccagg gugagguagu aaguuguauu guugugggu agggauauua       60 ggccccaauu agaagauaac uauacaacuu acuacuuucc cuggugugug gcauauuca      119

<210> SEQ ID NO 4
<211> LENGTH: 22
<212> TYPE: RNA
<213> ORGANISM: Homo sapiens

<400> SEQUENCE: 4
ugagguagua aguuguauug uu                                              22

<210> SEQ ID NO 5
<211> LENGTH: 82
<212> TYPE: RNA
<213> ORGANISM: Homo sapiens

<400> SEQUENCE: 5 aggggggcgag ggauuggaga gaaaggcagu uccugauggu ccccucccca ggggcuggcu    60
uuccucuggu ccuucccucc ca                                              82

<210> SEQ ID NO 6
<211> LENGTH: 22
<212> TYPE: RNA
<213> ORGANISM: Homo sapiens

<400> SEQUENCE: 6
uggagagaaa ggcaguuccu ga                                              22
```

<210> SEQ ID NO 7
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 7
gcatactccg accgttactt cagaccg                                27

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ggtgccattg cacttgtctc                                        20

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
tcagcatact ccgaccgtta ct                                     22

<210> SEQ ID NO 10
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 10
ggcgtaataa tcgctccatt caacaataca a                           31

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 11
cgcaagaagt gaggtagtaa gttg                                   24

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
cggcgtaata atcgctccat tc                                     22

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 13
caatggagag aaaggcagtt cc            22

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
aatccatgag agatccctac cg            22

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
tggagagaaa ggcagttcct            20

<210> SEQ ID NO 16
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 16
tggtttaccg tcccac            16

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 17
ttcagctcct atatgatg            18

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
tagtagaccg tatagcgta            19

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 19
tatgtaacac ggtccacta            19

<210> SEQ ID NO 20

```
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 20
ctggcccgag ggacc                                                    15

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
atataataca acctgctaag                                               20

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 22
tggtagacta tggaacgta                                                19

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 23
gaacggcgtc atgcaggag                                                19

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
aacacaccca gctaaccttt                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
cacagctccc atctcagaac                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
```
tacagttgtt caaccagtta                                                20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
tacagttgtt caaccagtta                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
tgaggtagta agttgtattg                                                20

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29
tgaggttggt gtactgtgtg t                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
atcaacagac attaattggg c                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 31
aggttacccg agcaactttg c                                              21

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 32
aaggttactt gttagttca                                                 19

<210> SEQ ID NO 33
<211> LENGTH: 20
<212> TYPE: DNA

-continued

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
cctcccacac ccaaggcttg                                               20

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34
aatgacacga tcactcccgt t                                             21

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
cattgcactt gtctcggtct                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
cgcttcggca gcacatatac                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
ttcacgaatt tgcgtgtcat                                               20

<210> SEQ ID NO 38
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 38
gtacagctgt tgacagtgag cgactggaga gaaaggcagt tcctgatgtg aa           52

<210> SEQ ID NO 39
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 39
gccacagatg gtcaggaact ctttctctcc agctgcctac tgcctcggaa              50

```
<210> SEQ ID NO 40
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 40
ccatctgtgg cttcacatca ggaactgcct ttctctccag tcgctcactg tcaacagct         59

<210> SEQ ID NO 41
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 41
agctttccga ggcagtaggc agctggagag aaagagttcc tga                          43

<210> SEQ ID NO 42
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 42
gtacagctgt tgacagtgag cgacaggcgg agacttgggc aattgctgtg aa                52

<210> SEQ ID NO 43
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 43
gccacagatg ggcaattgcc agtctccgcc tgctgcctac tgcctcggaa                   50

<210> SEQ ID NO 44
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 44
ccatctgtgg cttcacagca attgcccaag tctccgcctg tcgctcactg tcaacagct         59

<210> SEQ ID NO 45
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 45
agctttccga ggcagtaggc agcaggcgga gactggcaat tgc                          43
```